United States Patent
Masini

(10) Patent No.: US 7,419,491 B2
(45) Date of Patent: Sep. 2, 2008

(54) BONE-CONSERVING ORTHOPEDIC INSTRUMENTATION AND APPLIANCES

(75) Inventor: Michael A. Masini, Ann Arbor, MI (US)

(73) Assignee: MedIdea, LLC, Ann Arbor, MI (US)

( * ) Notice: Subject to any disclaimer, the term of this patent is extended or adjusted under 35 U.S.C. 154(b) by 837 days.

(21) Appl. No.: 10/685,620

(22) Filed: Oct. 15, 2003

(65) Prior Publication Data

US 2004/0078042 A1    Apr. 22, 2004

Related U.S. Application Data

(60) Continuation-in-part of application No. 10/308,046, filed on Dec. 2, 2002, now Pat. No. 7,128,745, which is a division of application No. 09/159,168, filed on Sep. 23, 1998, now Pat. No. 6,488,687, said application No. 10/308,046 is a continuation-in-part of application No. 09/300,665, filed on Apr. 27, 1999, now Pat. No. 6,602,259, which is a continuation of application No. 08/937,216, filed on Sep. 18, 1997, now Pat. No. 5,897,559.

(60) Provisional application No. 60/059,804, filed on Sep. 23, 1997.

(51) Int. Cl.
  *A61F 5/00* (2006.01)
  *A61B 17/58* (2006.01)

(52) U.S. Cl. ............................. 606/87; 606/88

(58) Field of Classification Search ............. 623/20.16; 606/82, 86–89
See application file for complete search history.

(56) References Cited

U.S. PATENT DOCUMENTS

| | | | |
|---|---|---|---|
| 3,868,730 A | 3/1975 | Kaufer et al. ...................... 3/1 |
| 4,736,737 A | 4/1988 | Fargie et al. .................... 623/20 |
| 4,738,253 A | 4/1988 | Buchel et al. ................. 128/92 |
| 4,893,619 A | 1/1990 | Dale et al. ..................... 606/87 |
| 4,936,847 A | 6/1990 | Manginelli .................... 623/23 |
| 4,938,769 A | 7/1990 | Shaw .......................... 623/20 |
| 4,944,757 A | 7/1990 | Martinez et al. .............. 623/20 |
| 4,944,760 A | 7/1990 | Kenna .......................... 623/20 |
| 4,979,949 A | 12/1990 | Matsen, III et al. ........... 606/88 |
| 5,021,056 A | 6/1991 | Hofmann et al. .............. 606/53 |
| 5,047,058 A | 9/1991 | Roberts et al. ............ 623/20.16 |
| 5,092,869 A | 3/1992 | Waldron ....................... 606/82 |
| 5,122,144 A | 6/1992 | Bert et al. ..................... 606/88 |
| 5,129,909 A | 7/1992 | Sutherland ................... 606/88 |
| 5,226,915 A | 7/1993 | Bertin ......................... 623/20 |
| 5,234,433 A | 8/1993 | Bert et al. ..................... 606/88 |
| 5,236,432 A | 8/1993 | Masten, III et al. ........... 606/88 |

(Continued)

*Primary Examiner*—Bruce Snow
(74) *Attorney, Agent, or Firm*—Gifford, Krass, Sprinkle, Anderson & Citkowski, PC

(57) ABSTRACT

Apparatus and surgical techniques provide alternative cutting fixtures and other features to improve bone resection accuracy and joint stability. According to one embodiment, stabilizers are removably attached to a cutting guide to temporarily lengthen the surface against which a saw or other cutting device rests. Another embodiment provides differently shaped saw blades, having curved distal ends and right-angle bends applicable to box cuts of the type associated with cruciate sacrifice knee-replacement surgery. Methods are also disclosed whereby the box cuts, distal and posterior augment cuts may be approached from a distal perspective, both laterally and medially. A different embodiment provides a trial/cutting guide having flat surfaces as opposed to curved surfaces adapted for articulation within a joint. Yet a further alternative embodiment teaches a device for determining the joint line relative to a tibia using the fibula as reference.

23 Claims, 4 Drawing Sheets

U.S. PATENT DOCUMENTS

| | | | | |
|---|---|---|---|---|
| 5,250,050 | A | 10/1993 | Poggie et al. | 606/79 |
| 5,258,032 | A | 11/1993 | Bertin | 606/88 |
| 5,263,498 | A | 11/1993 | Caspari | 623/20 |
| 5,275,603 | A | 1/1994 | Ferrante et al. | 606/86 |
| 5,282,866 | A | 2/1994 | Cohen et al. | 623/20 |
| 5,342,367 | A | 8/1994 | Ferrante et al. | 606/86 |
| 5,364,401 | A | 11/1994 | Ferrante et al. | 606/84 |
| 5,364,402 | A | 11/1994 | Mumme et al. | 606/88 |
| 5,423,827 | A | 6/1995 | Mumme | 606/87 |
| 5,458,645 | A | 10/1995 | Bertin | 623/20 |
| 5,464,406 | A | 11/1995 | Ritter et al. | 606/86 |
| 5,474,559 | A | 12/1995 | Bertin et al. | 606/86 |
| 5,490,854 | A | 2/1996 | Fisher et al. | 606/88 |
| 5,514,139 | A | 5/1996 | Goldstein et al. | 606/79 |
| 5,569,259 | A | 10/1996 | Ferrante et al. | 606/86 |
| 5,597,379 | A | 1/1997 | Haines et al. | 606/80 |
| 5,601,563 | A | 2/1997 | Burke | 606/86 |
| 5,643,272 | A | 7/1997 | Haines et al. | 606/80 |
| 5,662,656 | A | 9/1997 | White | 606/86 |
| 5,683,397 | A | 11/1997 | Vendrely et al. | 606/88 |
| 5,688,282 | A | 11/1997 | Baron | 606/86 |
| 5,702,460 | A | 12/1997 | Carls | 623/20 |
| 5,709,689 | A | 1/1998 | Ferrante et al. | 606/86 |
| 5,716,361 | A | 2/1998 | Masini | 606/86 |
| 5,720,752 | A | 2/1998 | Elliott | 606/87 |
| 5,722,978 | A | 3/1998 | Jenkins | 606/87 |
| 5,755,803 | A | 5/1998 | Haines et al. | 623/20 |
| 5,810,827 | A | 9/1998 | Haines et al. | 606/80 |
| 5,879,354 | A | 3/1999 | Haines et al. | 606/86 |
| 5,879,393 | A * | 3/1999 | Whiteside et al. | 623/22.4 |
| 5,897,559 | A | 4/1999 | Masini | 606/86 |
| 5,916,220 | A | 6/1999 | Masini | 606/87 |
| 5,947,973 | A | 9/1999 | Masini | 606/87 |
| 5,957,926 | A | 9/1999 | Masini | 606/87 |
| 5,980,526 | A * | 11/1999 | Johnson et al. | 606/86 |
| 6,056,754 | A | 5/2000 | Haines et al. | 606/80 |
| 6,197,064 | B1 | 3/2001 | Haines et al. | 623/20.31 |
| 6,602,259 | B1 | 8/2003 | Masini | 606/87 |
| 2002/0029038 | A1 | 3/2002 | Haines | 606/54 |

* cited by examiner

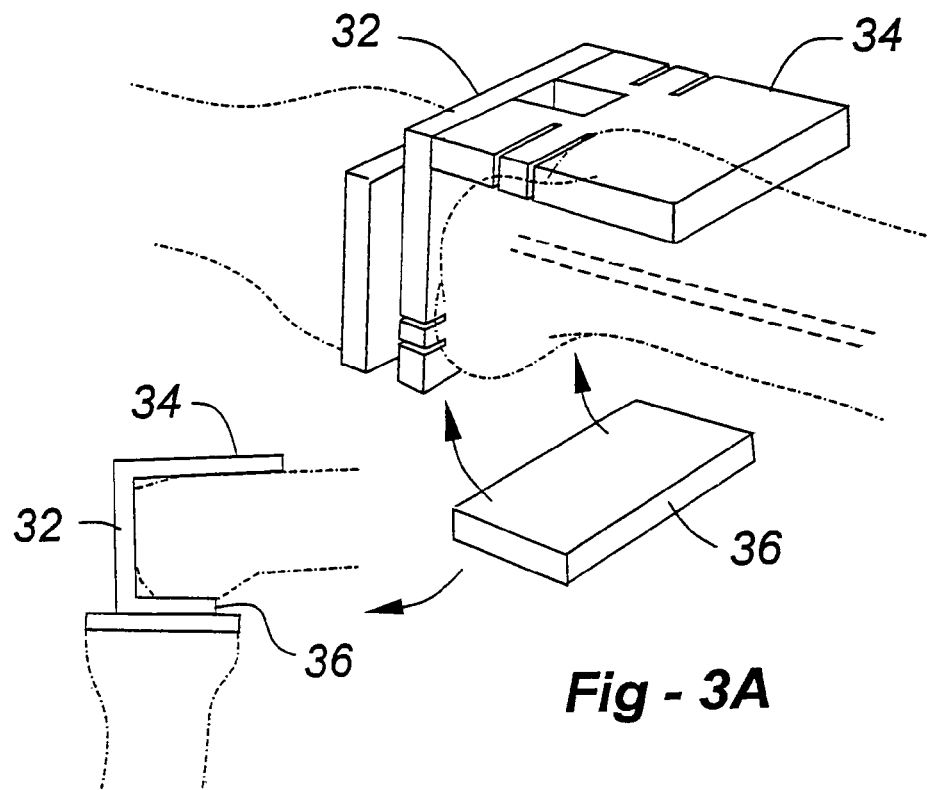
Fig - 3A
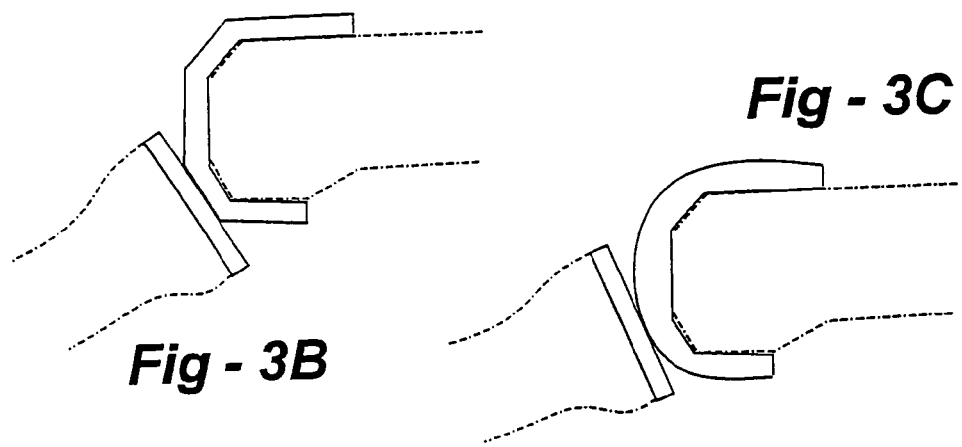
Fig - 3B
Fig - 3C

BONE-CONSERVING ORTHOPEDIC INSTRUMENTATION AND APPLIANCES

REFERENCE TO RELATED APPLICATIONS

This application is a continuation-in-part of U.S. patent application Ser. No. 10/308,046, filed Dec. 2, 2002; which is a divisional of U.S. patent application Ser. No. 09/159,168, filed Sep. 23, 1998, now U.S. Pat. No. 6,488,687; which claims priority of U.S. provisional patent application Ser. No. 60/059,804, filed Sep. 23, 1997. U.S. patent application Ser. No. 10/308,046 is also a continuation-in-part of U.S. patent application Ser. No. 09/300,665, filed Apr. 27, 1999, now U.S. Pat. No. 6,602,259, which is a continuation of U.S. patent application Ser. No. 08/937,216, filed Sep. 18, 1997, now U.S. Pat. No. 5,897,559, the entire content of all of which are incorporated herein by reference.

FIELD OF THE INVENTION

This invention concerns arthroplasty, and, more particularly, resides in improved cutting guides and techniques to better assist a surgeon in preparing a bone, for example, to receive an implant.

BACKGROUND OF THE INVENTION

Whether for primary or revision arthroplasty, cutting guides are typically employed to ensure that the bone saw performs resections corresponding to mating surfaces of the prosthetic component. For example, in a femoral knee replacement, cutting guides or blocks are temporarily secured to the distal end of the femoral shaft, and include slots into which the blade of an oscillating saw is inserted to shape the end of the bone in accordance with corresponding surfaces of the prosthetic element.

In the case of a revision, the procedure is usually more elaborate due to deterioration of the previously prepared surfaces resulting from decomposition of the bone/prosthesis interface, necrosis, and other factors. Cutting blocks are also typically used in revision procedures, though bone deficiency often renders stabilization of the block impossible. In addition, if the cutting block includes a stem, the positioning of the stemmed implant can alter the fit of the final prosthesis relative to the bone. More recently introduced techniques attempt to base the cuts on an intramedullary guide to which additional cutting blocks are mounted. Though such approaches improve bone cutting accuracy, there remains an unacceptable margin of error, the correction of which in some cases requiring a freehand shaping of the bone.

SUMMARY OF THE INVENTION

This invention extends and, in certain instances, improves upon, apparatus and methods disclosed and claimed in U.S. Pat. No. 5,716,361, which relates to combination trial/cutting guides, and methods of using the same, in various orthopedic joint situations such as the knee, hip, shoulder, and other areas of the body. The present invention is directed toward apparatus and surgical techniques which augment or supplant certain teachings of the '361 patent with respect to alternative cutting fixtures and resection accuracy and stability.

One embodiment provides stabilizers which are removably attached to a cutting guide so as to temporarily lengthen the surface against which a saw or other cutting device rests. Another embodiment provides differently shaped saw blades, having curved distal ends and right-angle bends applicable to box cuts of the type associated with cruciate-sacrifice knee-replacement surgery. Methods are also disclosed whereby the box cuts, distal and posterior augment cuts may be approached from a distal perspective, both laterally and medially. A different embodiment provides a trial/cutting guide having flat surfaces as opposed to curved surfaces adapted for articulation within a joint. Yet a further alternative embodiment teaches a device for determining the joint line relative to a tibia using the fibula as reference.

BRIEF DESCRIPTION OF THE DRAWINGS

FIG. 3A is a drawing which depicts a trial/cutting guide having flat surfaces as opposed to curved surfaces adapted for articulation within a joint;

FIG. 3B is a drawing which depicts a trial/cutting guide having truncated surfaces corresponding to chamfer cuts;

FIG. 3C is a drawing which depicts a trial/cutting guide having a rounded surface;

DETAILED DESCRIPTION OF THE INVENTION

The present invention extends and, in certain instances, improves upon apparatus and methods disclosed and claimed in U.S. Pat. No. 5,716,361, which issued Feb. 10, 1998, entitled BONE CUTTING GUIDES FOR USE IN THE IMPLANTATION OF PROSTHETIC JOINT COMPONENTS. Accordingly, the entire contents of this patent are incorporated herein by reference. Broadly, the '361 patent relates to combination trial/cutting guides, and methods of using the same, in various orthopedic joint situations such as the knee, hip, shoulder, and other areas of the body. The apparatus resides in a shaped body having an inner surface adapted for temporary placement against a bone surface and an outer surface configured to co-act in a joint, for example, as part of a trial reduction. The present invention is directed toward apparatus and surgical techniques which augment or supplant certain teachings of the '361 patent with respect to alternative cutting fixtures and resection accuracy and stability. The various aspects of the instant disclosure are broadly classified according to broad categories which follow.

Trial/Cutting Guide Stabilizers

In some instances, including those associated with femoral knee arthroplasty, the shaping of the cutting body to co-act in a joint may result in relatively thin thicknesses between the inner and outer surfaces of the body. As such, if surfaces or slots are provided for a particular resection, the cutting tool may extend through the body of the device for only a short distance, resulting in a potential instability.

This aspect of the present invention is accordingly directed toward the lengthening of one or more of the cutting guides through the use of removable stabilizers which are temporarily attached to the body. This feature builds upon concepts disclosed in reference to FIG. 6 of the '361 patent, in particular, which teaches the use of an extension block to carry out box cuts. However, although the following discussion and drawings reference a combination trial and cutting guide of the type disclosed in this issued patent, it should be understood that these removable stabilizers are applicable to other bone-cutting situations and, in fact, may be applied to cutting guides even if they are not shaped to function as a trial device.

Figure 1:
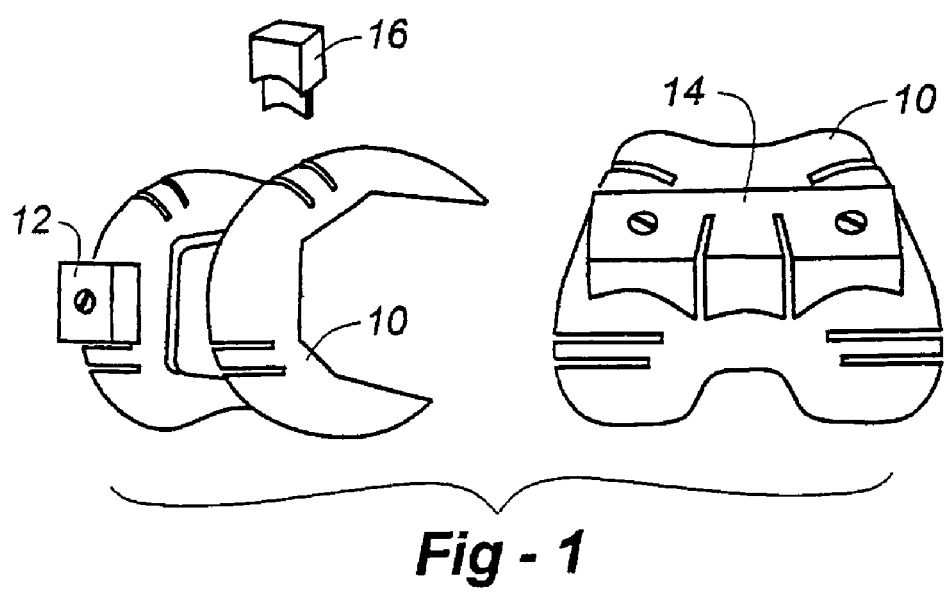
FIG. 1 is a drawing which shows the use of stabilizers removably attached to a cutting guide to temporarily lengthening the surface against which a saw or other cutting device uses as a guide.

As illustrated in FIG. 1, stabilizers 12 and 14 are temporarily and removably attached to a cutting guide 10, thereby effectively lengthening the surface against which a saw or other cutting device uses as a guide with respect to a resection procedure. The stabilizers may include a single, extended flat surface such as that provided by block 12, or may include slots, as shown with respect to block 14, or both surfaces and slots in combination with additional features.

The stabilizers may be temporarily affixed to the cutting guide in a number of ways, including removable machine screws or Allen screws, or detachable snaps which use pressure to apply and remove the members. As a further alternative, a stabilizer such as 16 may include a feature which fits into an adjacent slot to provide temporary positioning. The application of the stabilizers according to the invention is not limited to the slots, openings or positions illustrated in the drawing, but may be used in conjunction with any provided cutting surface. Procedurally, the method of use would follow that disclosed in the '361 patent, in that a reduction would be performed and, upon a successful trial, the resections would be carried, as required, with the addition of these slot extensions being used for further tool stabilization as disclosed herein.

Saw Blades for Effective Box-cut Resections

In U.S. Pat. No. 5,716,361, slots and surfaces are provided to perform box cuts of the type associated with a cruciate-sacrificing procedure. Apparatus and methods are shown whereby even the bottom of the box could be at least partially formed by a slot or surface provided for such purpose. Although the end of the saw blade may eventually reach the surface of an intramedullary stem, if so provided, upon removal of interfering portion later in the procedure, the beginning of the cut could simply be extended, using the cut itself as a guide for the remaining portion of the resection.

Figure 2A:
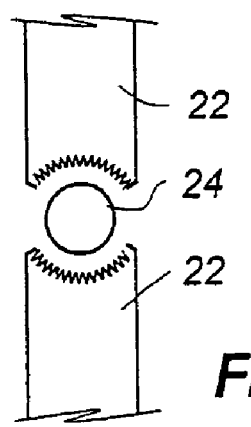
FIG. 2A is a drawing of a curved saw blade according to the invention
Figure 2B:
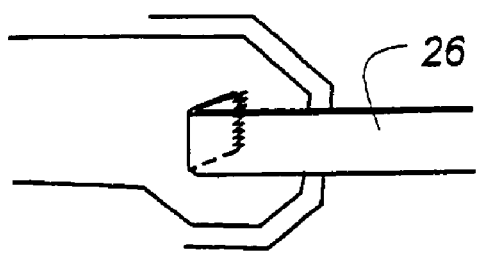
FIG. 2B is a drawing of an alternative saw blade according to the invention, preferably including a right-angle bend.

As shown in FIG. 2A, a curved saw blade 22 may be provided such that when the stem 24 is approached from above or below, additional material on either side of the stem will be more effectively removed, thereby forming nearly the entire bottom of the box even with the stem in place. As an alternative to posterior-anterior slot orientation, a different or supplemental set of slots may be provided to approach the bottom cut from the side of the trial-guide body. As shown in FIG. 2B, a saw 26 having a right-angle blade may be provided, such that and with the trial/cutting guide in place and with the knee flexed, any remaining portion(s) of the bottom of the box may be approached from the side.

Geometric Trial/Cutting Guides

A different aspect of this invention is directed toward trial/cutting guides which do not necessarily include articulating outer surfaces to co-act in a joint. That is, in contrast to certain of the devices and techniques disclosed in U.S. Pat. No. 5,716,361 wherein, for example, condylar surfaces are provided to co-act in a joint, so long as both sides of the joint have surfaces which mate to properly determine gaps or distances, such surfaces which conform to human anatomy need not be provided as a prelude to a trial joint reduction.

As shown in FIGS. 3A-3C, trial/cutting guides may be provided having surfaces geometrically indexed to a final implant, as opposed to complex, curved articulating surfaces, and still function to establish a desired orientation as part of a trial joint reduction. As long as the opposite side of the joint is configured to mate with these flat surface, the surgeon may reduce this assembly into the joint to test for proper joint action, including extension/flexion gaps in the case of knee-replacement surgery. With the trial/cutting guide is in position, it may be moved around so as to mate with the corresponding joint surface and then pinned into place once a desired orientation has been established. After flexing, the cuts associated with the joint may be made with the cutting guide and, in the event that augments are required, these may be provided in conjunction with a trial or a final, as appropriate.

Although FIG. 3A shows a primary distal flat section which is connected to a stem and an anterior section, the apparatus may include a posterior section as depicted with the arrow. In such a case, when the joint is flexed, this posterior piece may rest against the tibial portion to stabilize the entire assembly for resection as shown in the small inset drawing. Nor do the test surfaces need to be flat or joined at right angles. As shown in FIG. 3B, the outer surface 38 may be truncated in a manner corresponding to the "chamfer" cuts or, alternatively, as shown in FIG. 3C, the outer surface 39 may be rounded off without having to form complex condylar surfaces, for example, so long as a geometric index is established with respect to the prosthesis ultimately installed in terms of joint line, flection/extension gaps, degree of varus/vulgus, or some combination of these or other criteria. One advantage of these alternative configurations is that joint geometry and movement may be tested for accuracy, but the apparatus may be much more easy to manufacture with the flat surfaces as opposed to highly complex surfaces used to provide natural joint features.

Alternative Cutting Approaches And Guide Marking

Figure 4A:
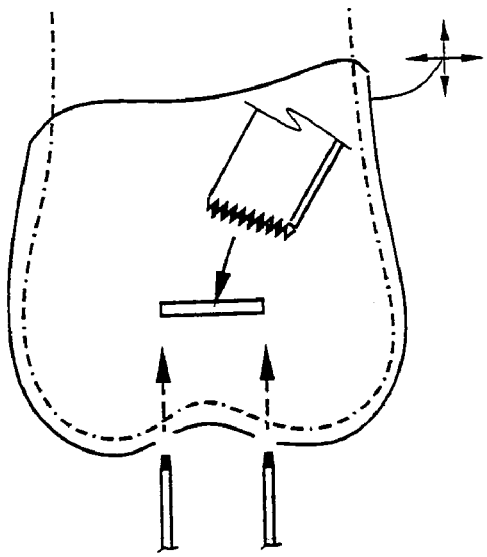
FIG. 4A is a drawing which illustrates a method of approaching box cuts from a distal perspective.

In performing cruciate sacrificing knee-replacement surgery, so-called box cuts are used to accommodate an intercondylar protrusion. To make the sides of the box cuts, slots may be provided from anterior to posterior, as shown in U.S. Pat. No. 5,716,361. As an alternative, however, slots may be provided as shown in FIG. 4A to approach these cuts distally. Although such a capability is disclosed in the form of an aperture in the '361 patent, slots may alternatively be provided, as shown.

Figure 4B:
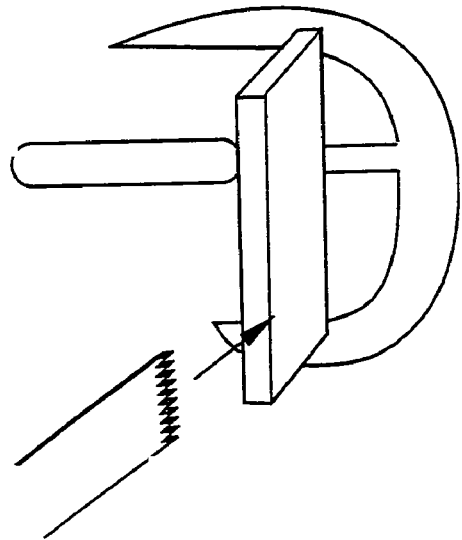
FIGS. 4B and 4C depict alternative ways in which distal and posterior augment cuts may be made from the side, whether laterally or medially.
Figure 4C:
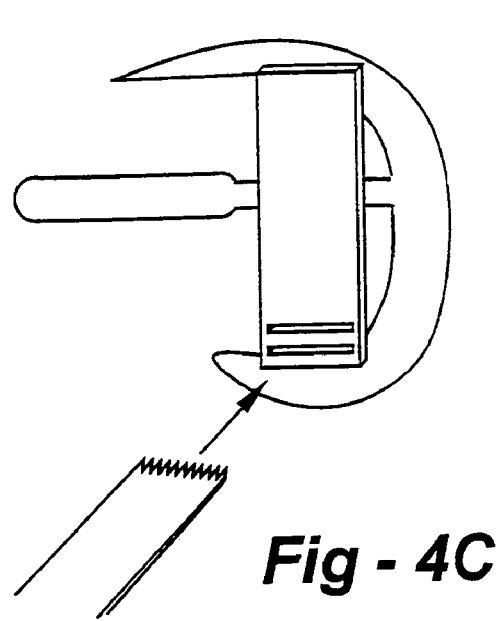

FIGS. 4B and 4C depict alternative ways in which the distal and posterior augment cuts may be made from the side, whether laterally or medially. FIG. 4B shows how a standard trial may be employed with or without other slots or cutting guides. In addition, a removable attachment guide may be temporarily attached to the side of the trial, as shown, to perform the distal cuts. The removable attachment guide may be located at different positions, depending upon the augments that will be used on the final.

As a further alternative, instead of a guide attachment, indicators may be provided along various edges or other points of the cutting guide body itself, enabling the surgeon to mark the bone, whether or not as part of a trial reduction, remove the cutting guide body, and perform the cuts in a conventional manner (i.e., with standard cutting guides). The advantage here, however, is that with the trial in place these markings would indicate precisely where the final implant will be fixed to the bone, whether augments are required or not. FIG. 4C illustrates a similar concept, except for the posterior cuts, in the sense that a standard trial could be used but again facilities could be provided whereby either a saw guide could be clipped on or the bone could be marked for the posterior and anterior cuts in the manner just described for the distal cut.

Fibula Referencing

Figure 5:
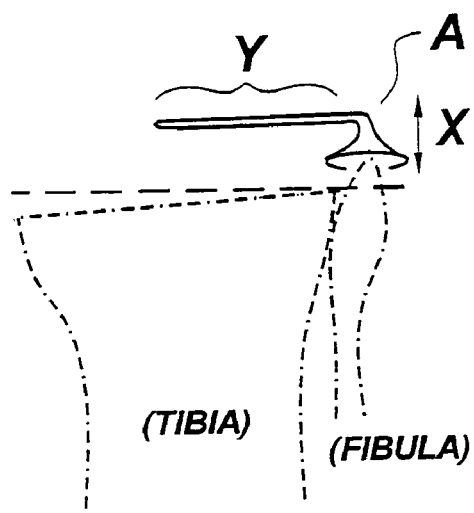
FIG. 5 shows a device for determining the joint line relative to a tibia using the fibula as reference.

FIG. 5 depicts a different aspect of the invention, including a device for determining the joint line relative to the tibia, using the fibula as reference. The device, labeled 'A', contacts the head or proximal portion of the fibula. The device preferably includes a transverse extending rod which is used to estimate where the joint line should be recreated relative to a deficient tibial surface. The vertical portion labeled 'X' may be adjustable or fixed. Adjustability allows the joint line to be estimated and adjusted relative to a different sized individual. This could be estimated from an x-ray or other means.

In addition, an element may be provided on the transverse bar 'Y', to assure a transverse positioning, such as a bubble within a fluid as commonly provided with a level, this of course would be more involved than just a simple transverse bar or any other such configuration would be appropriate as well.

Bone-loss Conforming Slots and Augments

Figure 6A:
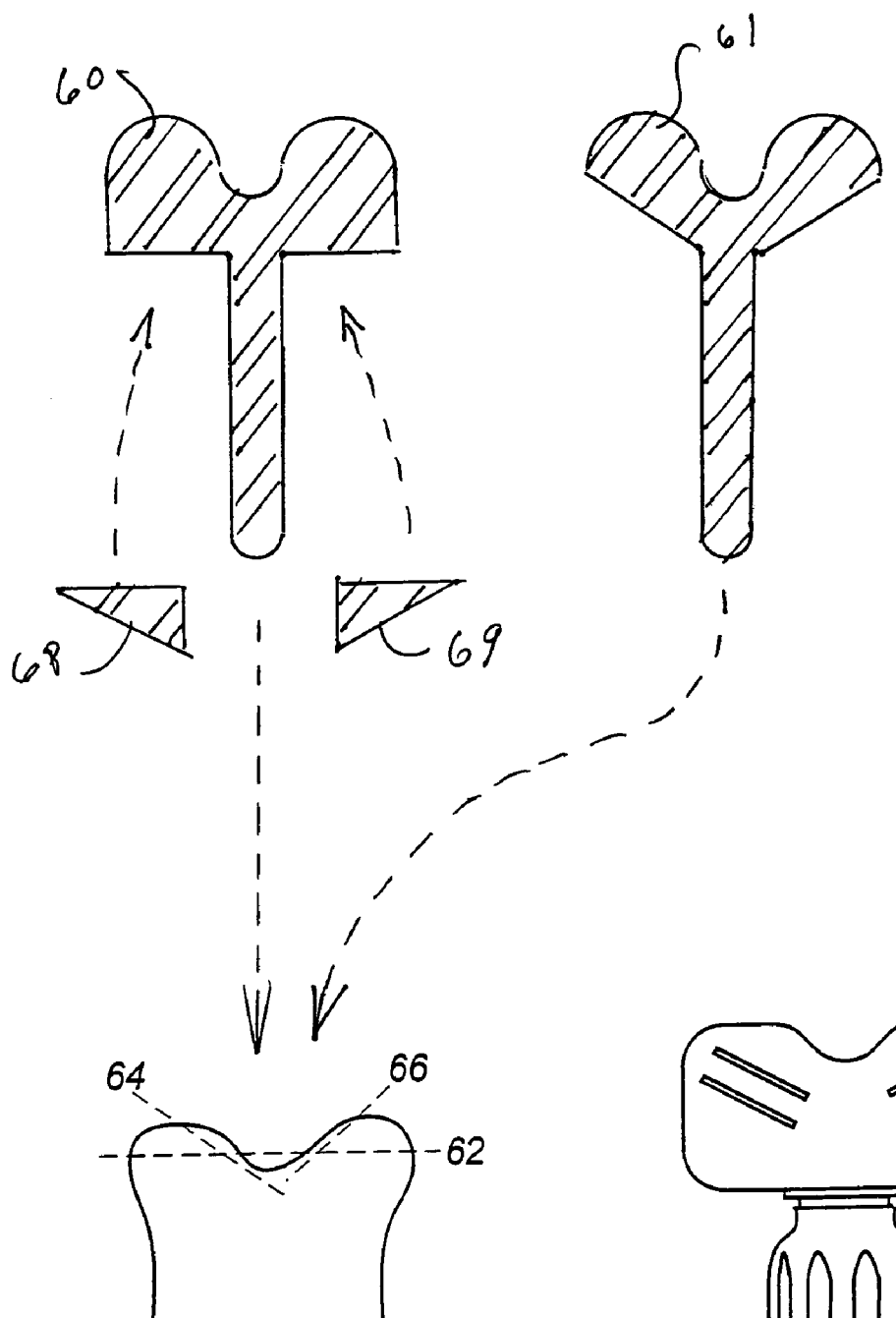
FIG. 6A is a drawing which shows a wedge-shaped defect often encountered in distal femur bone loss.

Now making reference to FIG. 6A, it is often the case that bone loss occurs primarily with respect to a central portion of the bone, leaving outer edges with a greater volume of bone stock remaining intact. As shown in FIG. 6A, such is typically the case with the distal femur, resulting in a defect which is often wedge-shaped, as shown. With traditional cutting guides that produce transversely-aligned surfaces, it is often the case that this abundance of medial and lateral remaining bone is simply resected and lost for the sake of geometric simplicity.

Figure 6B:
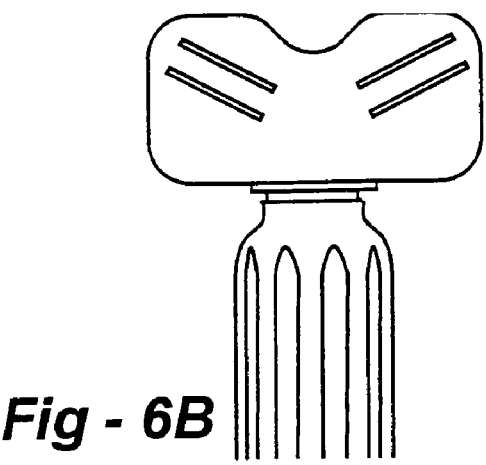
FIG. 6B is a drawing which shows a combination trial and cutting guide having "non-parallel" slots and wedges as part of a bone-loss conforming method of resection.

As shown in FIGS. 6A and 6B, a different aspect of this invention is the provision of non-parallel slots and corresponding prosthetic element 61, which may be used to retain at least some of this outer remaining bone material. That is, instead of making the traditional straight across distal cut 62, as shown in FIG. 6A, the cutting guide of FIG. 6B is instead used to make the cuts along lines 64 and 66 thereby retaining the tips of the outer portions of the bone. In the event that wedges are required to fill the gaps between the prosthetic element 60 and the surfaces created through these non-parallel slots, the wedges (68, 69) are also wedge-shaped. Although the specific example depicted has to do with the distal femur, it should be noted that the apparatus and methods are useful in any situation which would benefit from an oblique cut and/or corresponding wedges to conserve bone stock where, in the past, straight-across cuts have been used at the expense of such bone material.

I claim:

1. Bone-conserving orthopedic apparatus, comprising:
   a cutting guide for performing a set of lateral and medial resections, the cutting guide including:
   first and second saw-receiving slots, each slot being associated with a respective one of the lateral and medial resections, and wherein the resections resulting from the use of the slots slope inwardly along different planes from a respective outer medial and lateral surface.

2. The orthopedic apparatus of claim 1, wherein the lateral and medial resections are performed with respect to a pair of distal femoral condyles.

3. The orthopedic apparatus of claim 2, wherein the planes corresponding to the two resections intersect proximate to an intercondylar region.

4. The orthopedic apparatus of claim 2, wherein the two resections are performed as part of a distal resection of a human femur.

5. The orthopedic apparatus of claim 2, wherein the two resections are performed as part of a posterior resection of a human femur.

6. The orthopedic apparatus of claim 2, wherein the two resections are performed as part of an anterior resection of a human femur.

7. The orthopedic apparatus of claim 1, further including a prosthetic element having a set of bone-contacting surfaces corresponding to the resections.

8. The orthopedic apparatus of claim 1, adapted for use with an existing prosthetic element having co-planar lateral and medial bone-contacting surfaces, the apparatus further comprising:
   a pair of wedge-shaped augment elements, each shaped to consume the space between one of the resections and one of the bone-contacting surfaces.

9. Bone-conserving orthopedic apparatus, comprising:
   a cutting guide for a resecting a pair of lateral and medial protrusions, each protrusion having a sidewall sloping toward a central valley region, the cutting guide including:
   first and second saw-receiving slots the first slot being substantially conformal to the sidewall of one of the protrusions, and the other slot being substantially conformal to the sidewall of the other protrusion, and wherein the resections resulting from the use of the slots do not lie in the same plane.

10. The orthopedic apparatus of claim 9, wherein the protrusions are condyles.

11. The orthopedic apparatus of claim 9, wherein the resections intersect proximate to an intercondylar region.

12. The orthopedic apparatus of claim 9, wherein the two resections are performed as part of a distal resection of a human femur.

13. The orthopedic apparatus of claim 9, wherein the two resections are performed as part of a posterior resection of a human distal femur.

14. The orthopedic apparatus of claim 9, wherein the two resections are performed as part of an anterior resection of a human distal femur.

15. The orthopedic apparatus of claim 9, further including a prosthetic element having a set of bone-contacting surfaces corresponding to the resections.

16. The orthopedic apparatus of claim 9, adapted for use with an existing prosthetic element having co-planar lateral and medial bone-contacting surfaces, the apparatus further comprising:
   a pair of wedge-shaped augment elements, each shaped to consume the space between one of the resections and one of the bone-contacting surfaces.

17. Orthopedic apparatus for use with a bone having a longitudinal axis, the apparatus comprising:
   a cutting guide including a stem insertable into the bone in substantial alignment with the longitudinal axis; and at least one saw-receiving slot on the cutting guide for resecting the bone along a plane which is not transverse to the longitudinal axis.

18. The orthopedic apparatus of claim 17, wherein the bone is a human femur, and the stem is inserted into an intramedullary canal.

19. The orthopedic apparatus of claim 18, wherein the slot is used to perform a distal resection of the bone.

20. The orthopedic apparatus of claim 18, wherein the slot is used to perform an anterior resection of the bone.

21. The orthopedic apparatus of claim 18, wherein the slot is used to perform a posterior resection of the bone.

22. The orthopedic apparatus of claim 18, further including a prosthetic element having a bone-contacting surface corresponding to the resection.

23. The orthopedic apparatus of claim 18, adapted for use with an existing prosthetic element having a bone-contacting surface which is substantially transverse to the longitudinal axis, the apparatus further comprising:

a wedge-shaped augment element to consume the space between the resection and the bone-contacting surface.

* * * * *